United States Patent
Brockway (10) Patent No.: US 10,806,624 B2
(45) Date of Patent: Oct. 20, 2020

(54) MENSTRUAL CUPS AND RELATED METHODS

(71) Applicant: Lady Business LLC, Portland, OR (US)

(72) Inventor: Meagan Kennedy Brockway, Portland, OR (US)

(73) Assignee: Lady Business LLC, Portland, OR (US)

( * ) Notice: Subject to any disclaimer, the term of this patent is extended or adjusted under 35 U.S.C. 154(b) by 432 days.

(21) Appl. No.: 15/804,854

(22) Filed: Nov. 6, 2017

(65) Prior Publication Data
US 2018/0140458 A1    May 24, 2018

Related U.S. Application Data (60) Provisional application No. 62/424,278, filed on Nov. 18, 2016.

(51) Int. Cl.
*A61F 5/455*    (2006.01)

(52) U.S. Cl.
CPC .................................. *A61F 5/4553* (2013.01)

(58) Field of Classification Search
CPC .. A61F 5/44; A61F 5/451; A61F 5/455; A61F 5/4553; A61F 2005/4402
See application file for complete search history.

(56) References Cited

U.S. PATENT DOCUMENTS

| | | |
|---|---|---|
| 1,891,761 A | 12/1932 | Goddard |
| 2,061,384 A * | 11/1936 | Manegold ............. A61F 5/4553 604/330 |
| 2,089,113 A | 8/1937 | Chalmers |
| 2,534,900 A | 12/1950 | Chalmers |
| 3,404,682 A | 10/1968 | Waldron |
| 3,626,942 A | 12/1971 | Waldron |
| 3,845,766 A | 11/1974 | Zöller |
| D323,212 S | 1/1992 | Crawford |
| 5,827,248 A | 10/1998 | Crawford |
| D746,452 S | 12/2015 | Petrova |
| D760,897 S | 7/2016 | Teo |
| 2008/0077097 A1 | 3/2008 | Chambers et al. |
| 2010/0312204 A1 | 12/2010 | Sheu |
| 2015/0164680 A1 | 6/2015 | Chen |

(Continued)

OTHER PUBLICATIONS

Diva International, "Diva Cup," product information page from an ecommerce website on which the product is sold: www.cottonbabies.com/products/diva-international-the-diva-cup, available at least as early as Nov. 6, 2017.

(Continued)

*Primary Examiner* — Catharine L Anderson
(74) *Attorney, Agent, or Firm* — Dascenzo Intellectual Property Law, P.C.

(57) ABSTRACT

Menstrual cups comprise a resilient body having an open top and a closed bottom and defining an internal volume sized to hold menstrual fluid. The resilient body comprises a wall structure that extends from the open top to the closed bottom. The wall structure has an outer surface opposite the internal volume and an inner surface facing the internal volume. The resilient body is biased to an open conformation, and the resilient body has a longitudinal axis that extends through a center of the internal volume when in the open conformation.

19 Claims, 8 Drawing Sheets

(56) References Cited

U.S. PATENT DOCUMENTS

| | | |
|---|---|---|
| 2017/0049609 A1 | 2/2017 | Conti |
| 2017/0189222 A1 | 7/2017 | Lin |
| 2018/0028350 A1 | 2/2018 | Wilson et al. |
| 2019/0224039 A1* | 7/2019 | Garriga I Rodo .... A61F 5/4553 |

OTHER PUBLICATIONS

Intima, Lily Cup & Lily Cup Compact product information page: www.intima.com/en/lily_cups, available at least as early as Nov. 6, 2017.

MeLuna, Me Luna menstrual cups sample set order page: meluna-usa.com/index.php/where-to-buy/2013-11-19-04-53-49#!/MeLuna-EDUCATOR-Sample-Set/p/56855011/category=7122490, available at least as early as Nov. 6, 2017.

Lunette, "Lunette Menstrual Cup" product information page: store.lunette.com/products/lunette-menstrual-cup-violet, available at least as early as Nov. 6, 2017.

Rubycup, "Ruby Cup" product information page: shop.rubycup.com/shop/ruby-cup-sisterpack/, available at least as early as Nov. 6, 2017.

Anigan, "EvaCup" product information page, www.anigan.com/collections/eva-cup-products/products/anigan-evacup-single-pack, available at least as early as Nov. 6, 2017.

Fleurcup, "Fleurcup" product information page: www.fleurcup.com/default.htm, available at least as early as Nov. 6, 2017.

Super Jennie, "Super Jennie Menstrual Cup" product information page: www.superjennie.com/products/super-jennie-menstrual-cup, available at least as early as Nov. 6, 2017.

The Keeper, Inc., "The Keeper Cup" product information page: keeper.com/shop/the-keeper-cup/, available at least as early as Nov. 6, 2017.

The Keeper, Inc., "The Moon Cup" product information page: keeper.com/shop/the-moon-cup/, available at least as early as Nov. 6, 2017.

Yuuki, "Yuuki cup" product information page from an ecommerce website on which product is sold: menstrualcup.co/shop/products/Yuuki.html?lang=en, available at least as early as Nov. 6, 2017.

LENA, "LENA Cup" product information page: lenacup.com/products/lena-2-pack, available at least as early as Nov. 6, 2017.

Sckoon, "SckoonCup" product information page: www.sckoon.com/collections/clothmenstrualpads-menstrual-cup/products/sckooncup-soft-menstrual-cup-purple-zen, available at least as early as Nov. 6, 2017.

* cited by examiner

MENSTRUAL CUPS AND RELATED METHODS

RELATED APPLICATION

This application claims priority to U.S. Provisional Patent Application No. 62/424,278, entitled MENSTRUAL CUPS AND RELATED METHODS, which was filed on Nov. 18, 2016, and the complete disclosure of which is incorporated herein by reference.

FIELD

The present disclosure relates to menstrual cups.

BACKGROUND

Menstrual cups are devices worn inside the vagina during menstruation to catch menstrual fluid. Some users find menstrual cups to be uncomfortable, to be difficult to insert and remove, to be difficult to achieve a proper seal with the walls of the vagina for proper placement and use, and/or to be difficult to break the seal with the walls of the vagina for removal from the vagina.

SUMMARY

Menstrual cups and related methods are disclosed herein. Menstrual cups comprise a resilient body having an open top and a closed bottom and defining an internal volume sized to hold menstrual fluid. The resilient body comprises a wall structure that extends from the open top to the closed bottom. The wall structure has an outer surface opposite the internal volume and an inner surface facing the internal volume. The resilient body is biased to an open conformation. The resilient body has a longitudinal axis that extends through a center of the internal volume when in the open conformation.

In some examples, the wall structure comprises one or more continuous elongate ridges extending from the inner surface and circumscribing the wall structure not parallel to the open top.

In some examples, the resilient body is configured to be folded from the open conformation into a first folded conformation and a second folded conformation. In the first folded conformation, opposing sides of the wall structure are positioned generally adjacent each other and folded together along the longitudinal axis, and the wall structure imparts a first spring force in the first folded conformation. In the second folded conformation, opposing sides of the wall structure are positioned generally adjacent each other and folded together along the longitudinal axis, and the wall structure imparts a second spring force in the second folded conformation. The opposing sides in the second folded conformation are offset 90° from the opposing sides in the first folded conformation.

In some examples, at a first location on the outer surface of the wall structure a first distance away from the open top, impartation of a given force deforms the open top a first amount, and at a second location on the outer surface of the wall structure the first distance away from the open top and spaced from the first location by 90° about the longitudinal axis, impartation of the given force deforms the open top a second amount.

DESCRIPTION

Menstrual cups and related methods are disclosed herein. Generally, in the figures, elements that are likely to be included in a given example are illustrated in solid lines, while elements that are optional to a given example are illustrated in broken lines. However, elements that are illustrated in solid lines are not essential to all examples of the present disclosure, and an element shown in solid lines may be omitted from a particular example without departing from the scope of the present disclosure.

Figure 1:
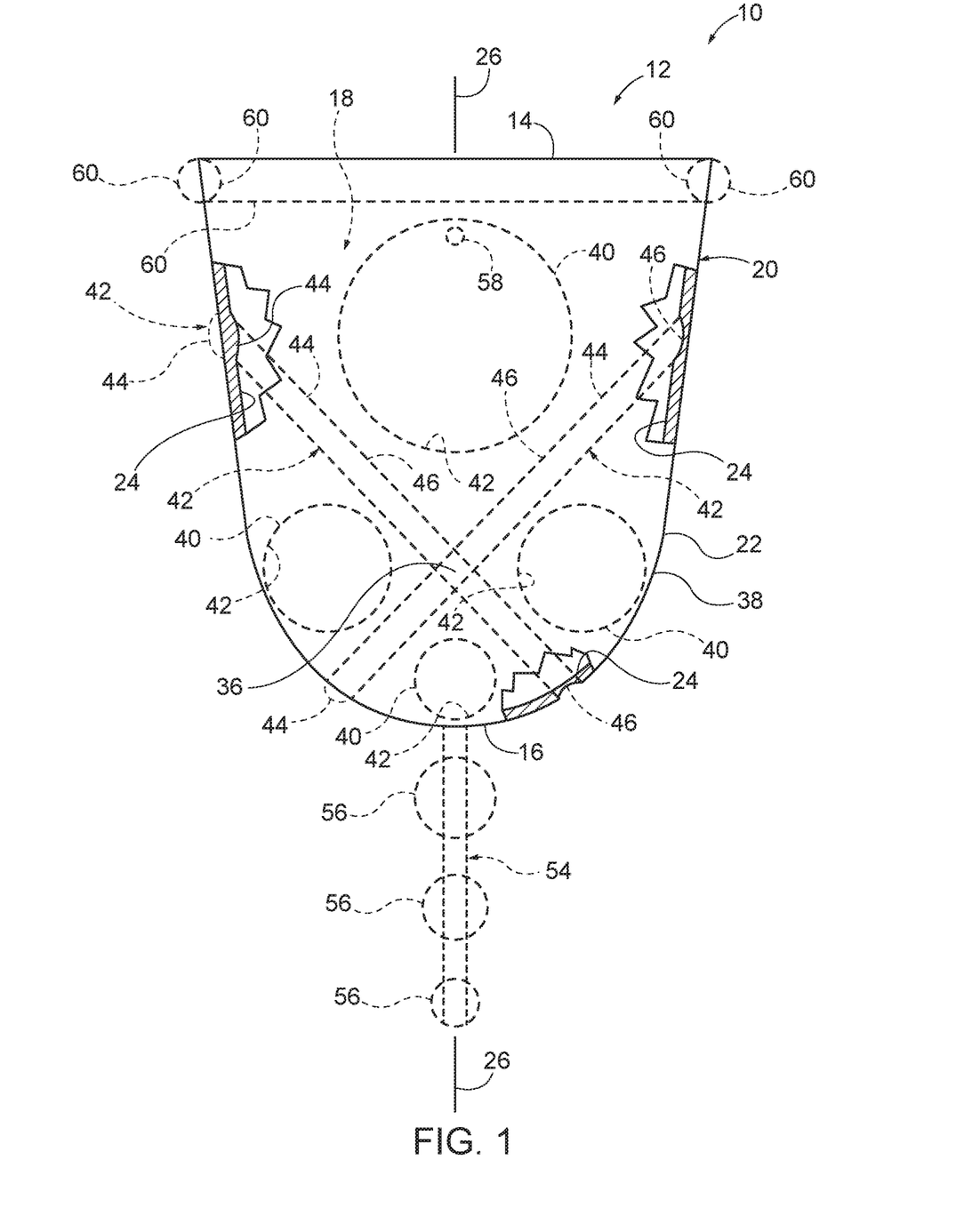
FIG. 1 is a schematic side view diagram representing menstrual cups according to the present disclosure.

Menstrual cups according to the present disclosure are schematically represented in FIG. 1 and indicated at 10. With reference to FIG. 1, menstrual cups 10 comprise at least a resilient body 12 having an open top 14 and a closed bottom 16. The resilient body 12 defines an internal volume 18 that is sized to hold menstrual fluid. As illustrative, non-exclusive examples, the internal volume 18 may be in the range of 20-50 milliliters (mL), but volumes outside of this range are within the scope of the present disclosure.

The resilient body 12 comprises a wall structure 20 that extends from the open top 14 to the closed bottom 16. The wall structure 20 has an outer surface 22 opposite the internal volume 18 and an inner surface 24 facing the internal volume 18. The resilient body is biased to an open conformation and has a longitudinal axis 26 that extends through a center of the internal volume 18 when in the open confirmation. The open conformation additionally or alternatively may be described as a default conformation or configuration and/or as a neutral, undeformed conformation or configuration.

The resilient body may be constructed of any suitable material, with silicone, medical grade silicone, rubber, gum rubber, and triphenylethylene (TPE) being illustrative, non-exclusive examples of suitable materials.

In some examples, menstrual cups 10 are configured to provide more than one degree, or level, of springiness, depending on how the resilient body 12 is folded for operative insertion into a vagina. For example, with reference to FIG. 2, a first folded conformation is represented in which opposing sides 28, 30 of the wall structure 20 are positioned generally adjacent each other and folded together along the longitudinal axis 26 of the resilient body 12. In such a first folded conformation, the resilient body 12 may be described as being deformed into a generally C- or U-shaped cross-section. Moreover, the first folded conformation may be described as a C-fold.

Figure 3:
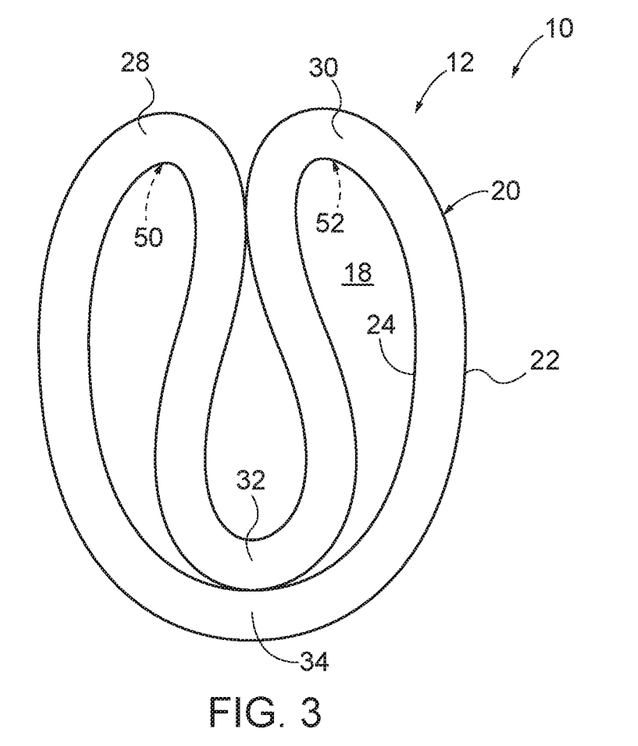
FIG. 3 is another schematic top view diagram representing menstrual cups according to the present disclosure in a folded conformation.
Figure 4:
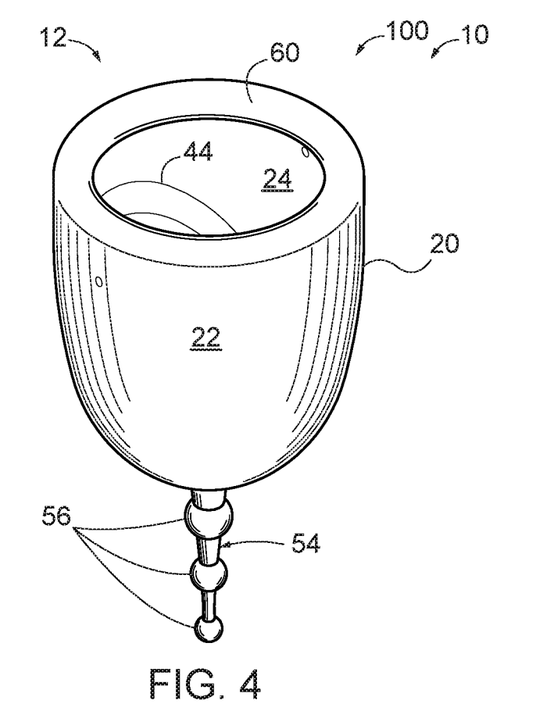
FIG. 4 is a perspective view of an illustrative, non-exclusive example of a menstrual cup according to the present disclosure.
Figure 5:
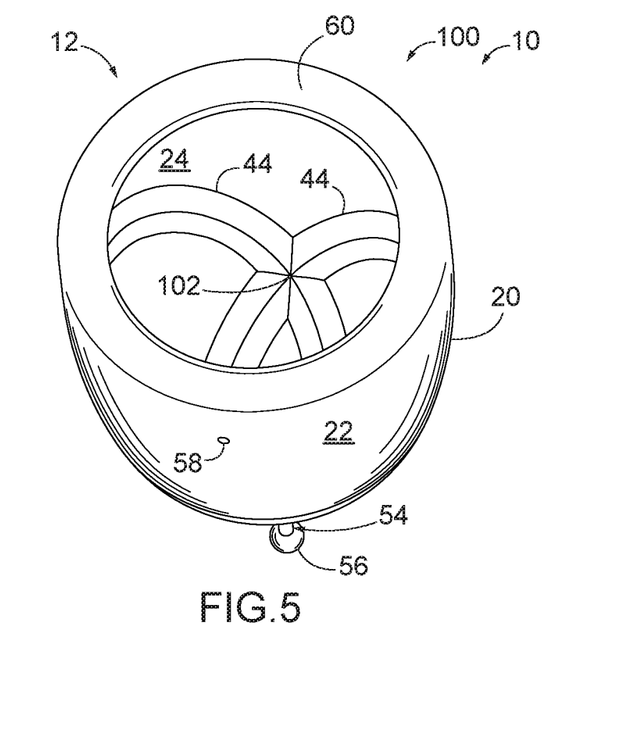
FIG. 5 is another perspective view of the menstrual cup of FIG. 4.
Figure 6:
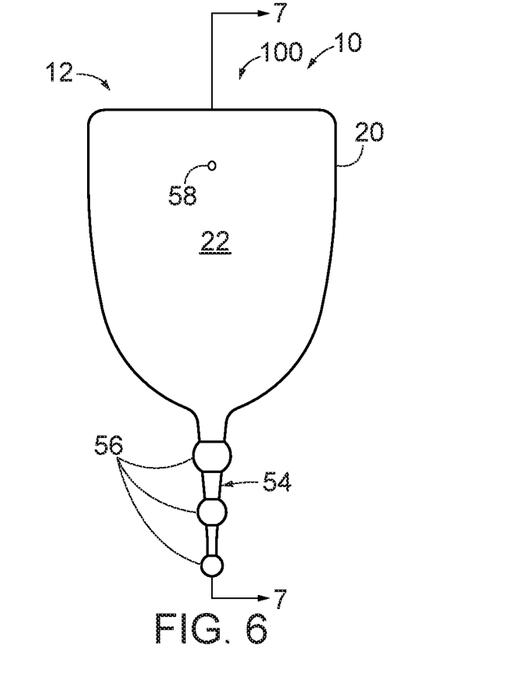
FIG. 6 is a side view of the menstrual cup of FIG. 4.
Figure 7:
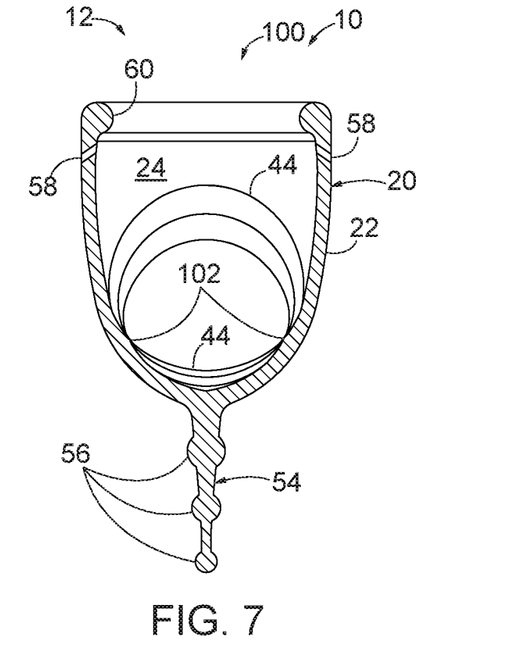
FIG. 7 is a cross-sectional view of the menstrual cup of FIG. 4, taken along the line 7-7 in FIG. 6.
Figure 8:
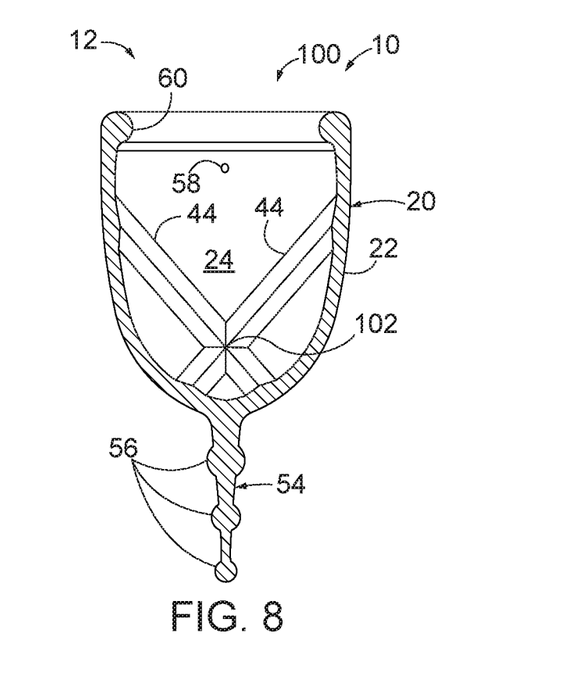
FIG. 8 is a cross-sectional view of the menstrual cup of FIG. 4, taken along the line 8-8 in FIG. 9.
Figure 9:
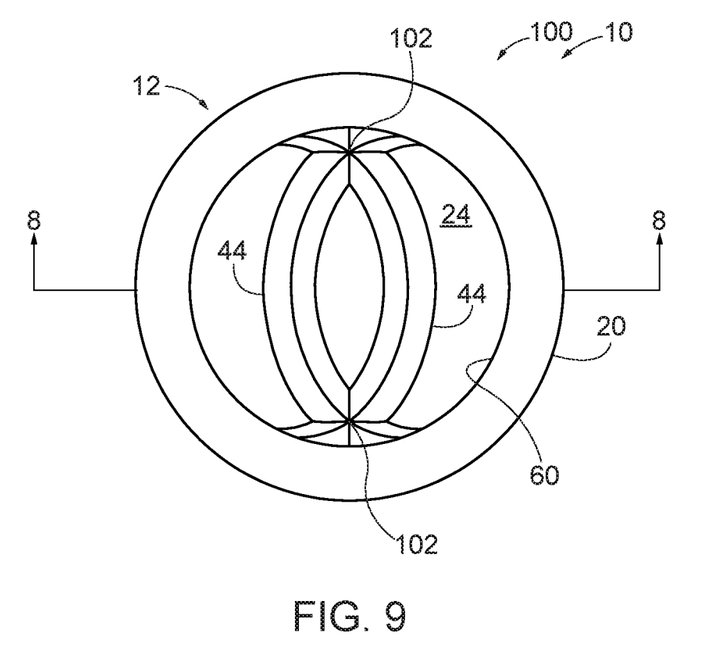
FIG. 9 is a top view of the menstrual cup of FIG. 4.
Figure 10:
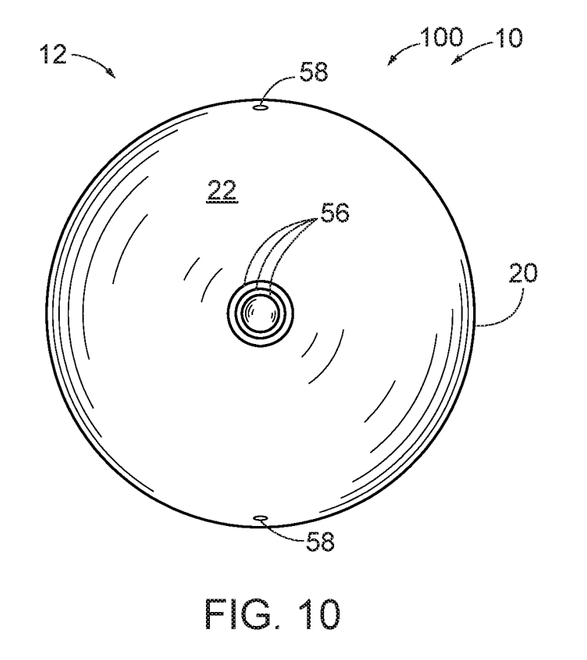
FIG. 10 is a bottom view of the menstrual cup of FIG. 4.
Figure 11:
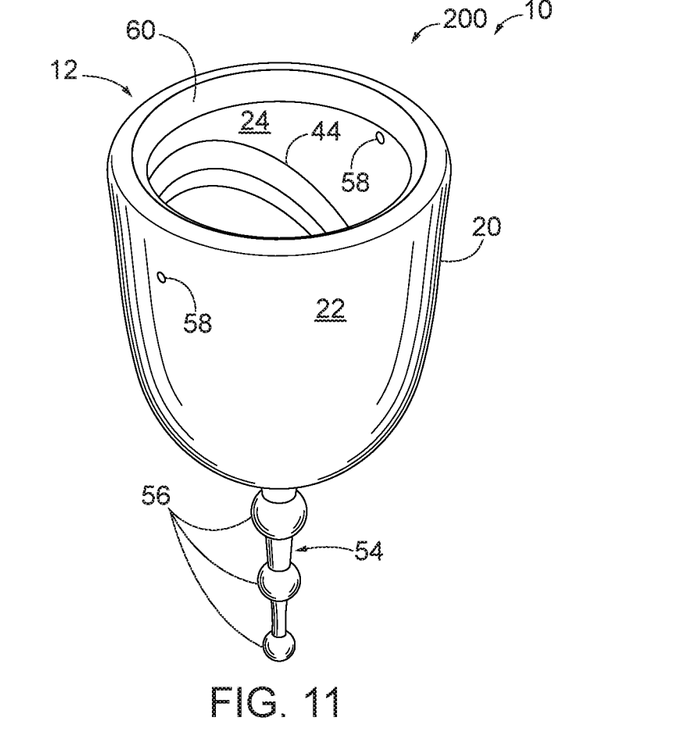
FIG. 11 is a perspective view of another illustrative, non-exclusive example of a menstrual cup according to the present disclosure.
Figure 12:
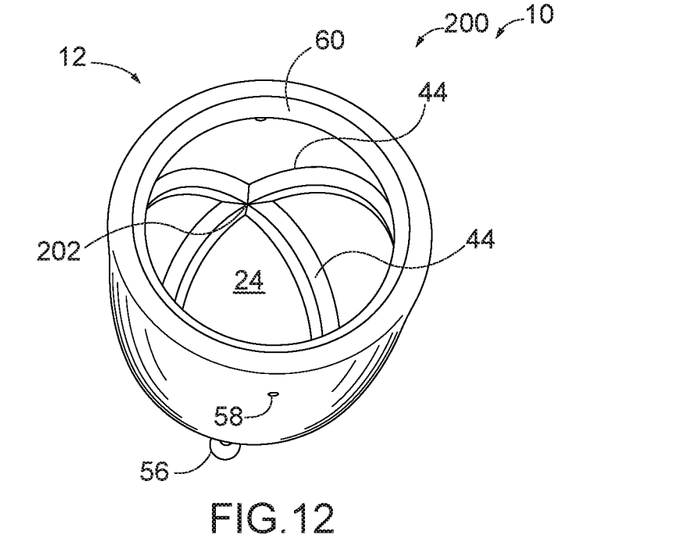
FIG. 12 is another perspective view of the menstrual cup of FIG. 11.
Figure 13:
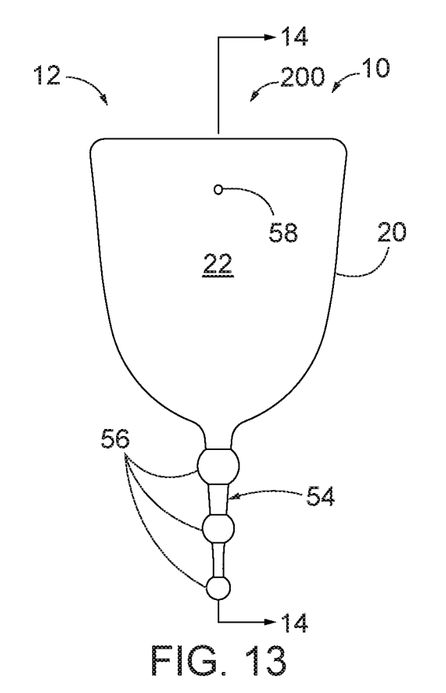
FIG. 13 is a side view of the menstrual cup of FIG. 11.
Figure 14:
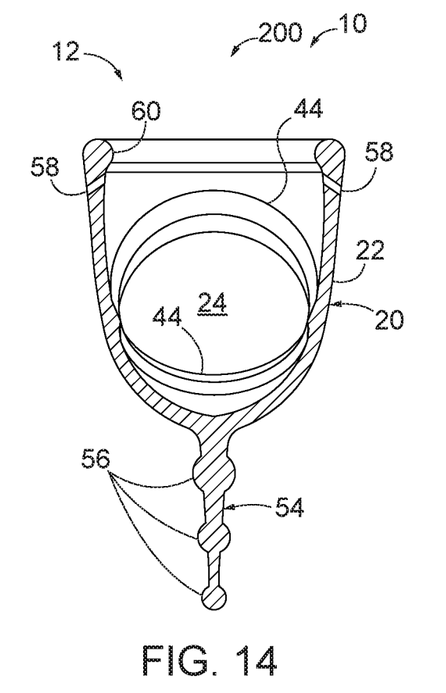
FIG. 14 is a cross-sectional view of the menstrual cup of FIG. 11, taken along the line 14-14 in FIG. 13.
Figure 15:
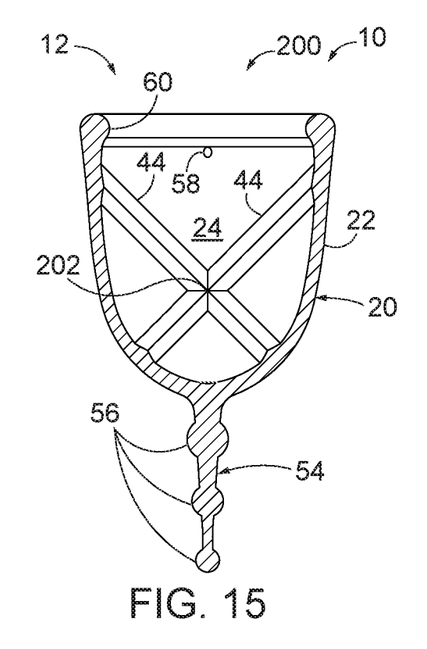
FIG. 15 is a cross-sectional view of the menstrual cup of FIG. 11, taken along the line 15-15 in FIG. 16.
Figure 16:
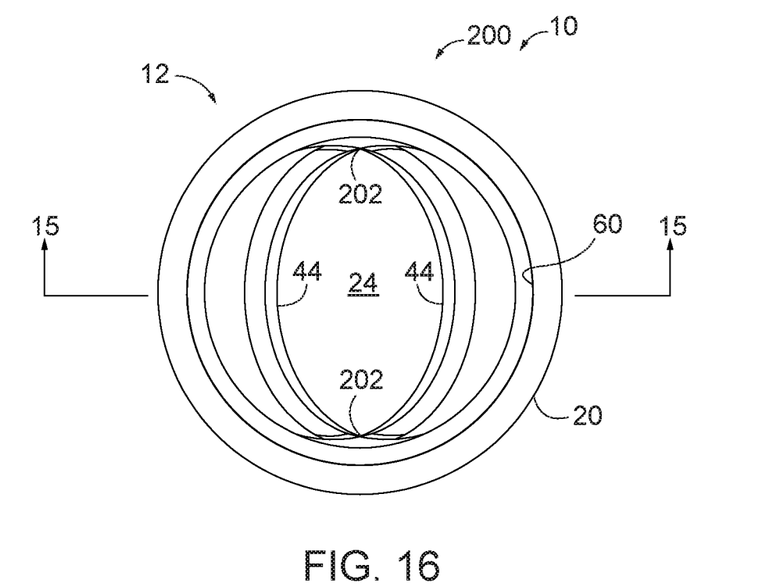
FIG. 16 is a top view of the menstrual cup of FIG. 11.
Figure 17:
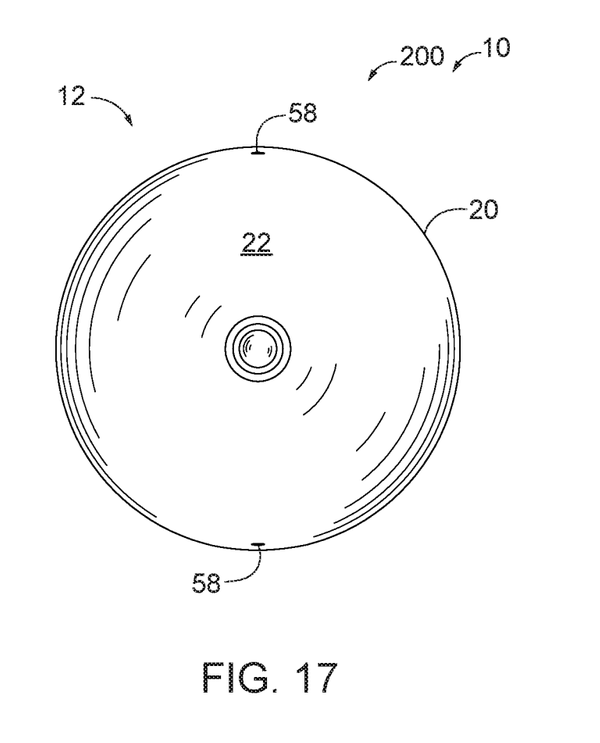
FIG. 17 is a bottom view of the menstrual cup of FIG. 11.

With reference to FIG. 3, a second folded conformation is represented in which opposing sides 32, 34 that are offset (e.g., 90° or generally 90°) from the opposing sides 28, 30 of the wall structure 20 are positioned generally adjacent each other and folded together along the longitudinal axis 26 of the resilient body 12. As with the first folded conformation, in the second folded conformation, the resilient body 12 may be described as being deformed into a generally C- or U-shaped cross-section, and the second folded conformation may be described as a C-fold.

In some such examples of menstrual cups 10, the wall structure 20 imparts spring force that is different in the first folded conformation than in the second folded conformation. That is, the internal bias of the resilient body 12 may be greater in one of the first and second folded conformations than in the other of the first and second folded conformations. Accordingly, a user of a menstrual cup 10 may select which folded conformation may be used when inserting the menstrual cup 10 into a vagina. For example, a greater spring force, or bias, may be desired to ensure that the resilient body 12 adequately reconforms to its open conformation and results in a proper seal with the walls of the vagina. On the other hand, a lesser spring force, or bias, may be desired to avoid a too forceful reconformation from a folded conformation to the open conformation.

Additionally or alternatively, some menstrual cups 10 are configured to provide more than one degree, or level, of deformation of the open top 14 for unsealing the menstrual cup 10 from the walls of a vagina, depending on how the resilient body 12 is deformed by a user when the menstrual cup 10 is operatively sealed with the walls of the vagina. For example, with reference back to FIG. 1, when a user imparts a given force at a first location 36 on the outer surface 22 of the wall structure 20, the open top 14 may deform to a greater extent than when a user imparts the same given force at a second location 38 on the outer surface 22 that is spaced from the first location (e.g., by 90° about the longitudinal axis 26) but the same distance away from the open top 14. Accordingly, in such examples, imparting a force to the first location may facilitate an easier unsealing of the menstrual cup 10 from the walls of the vagina.

With continued reference to the schematic representation of FIG. 1, in some examples of menstrual cups 10, the wall structure 20 has two or more thin regions 40 separated by one or more thick regions 42 or two or more thick regions 42 separated by one or more thin regions 40. In such examples, within the thin regions 40, the wall structure 20 has a thin wall thickness within a first thickness range, and within the thick regions 42, the wall structure 20 has a thick wall thickness within a second thickness range, and the first thickness range is less than the second thickness range. In FIG. 1, thin regions 40 are represented by dashed circles, schematically representing that thin regions 40 may be any suitable size and shape depending on a particular example of menstrual cup 10. That is, thin regions 40, while optionally being circular in shape, are not limited to being circular in shape. In FIG. 1, thin regions 40 also are schematically and optionally illustrated as being configured as elongate valleys 46, discussed in greater detail below. Thin regions 40 additionally or alternatively may be described as regions or zones of the wall structure 20 having a thickness that is less than thick regions 42. Similarly, in FIG. 1, thick regions 42 may be any suitable size and shape depending in a particular example of menstrual cup 10, with FIG. 1 also schematically illustrating thick regions 42 optionally configured as elongate ridges 44, discussed in greater detail below.

In some examples, the outer surface 22 of the wall structure 20 is smooth, such as schematically represented by the solid line defining the outer surface 22 in FIG. 1. In other words, in such examples, the thick regions 42 extend from the inner surface 24 of the wall structure 20 toward the internal volume 18 relative to directly adjacent thin regions 40, such as schematically represented in FIG. 1 in the cut-away section on the left with an optional elongate ridge 44 illustrated in cross-section.

In other examples of menstrual cups 10, the inner surface 24 is smooth. In other words, in such examples, the thick regions 42 extend from the outer surface 24 of the wall structure 20 away from the internal volume 18 relative to directly adjacent thin regions 40, such as optionally and schematically represented in FIG. 1 in dashed lines at the cut-away section on the left.

Any suitable number of thin regions 40 may be incorporated into a wall structure 20 of a menstrual cup 10. As illustrative, non-exclusive examples, a wall structure 20 may comprise 1-10, 2-10, 4-10, 6-10, 2-6, 2-4, or 4-6 thin regions 40. In some examples, a wall structure 20 consists of exactly 1, 2, 3, 4, 5, 6, 7, 8, 9, or 10 thin regions 40. Similarly, any suitable number of thick regions 42 may be incorporated into a wall structure 20 of a menstrual cup 10. As illustrative, non-exclusive examples, a wall structure 20 may comprise 1-10, 2-10, 4-10, 6-10, 2-6, 2-4, or 4-6 thick regions 42. In some examples, a wall structure 20 consists of exactly 1, 2, 3, 4, 5, 6, 7, 8, 9, or 10 thick regions 42.

In some examples, such as schematically illustrated at the cut-away sections on the right and lower right in FIG. 1, the thin regions 40 comprise one or more elongate valleys 46 that extend into the wall structure 20 relative to adjacent thick regions 42. In some such examples, the elongate valleys 46 extend in directions that are transverse to the open top 14, that is, are not parallel to the open top 14.

In some examples, such as schematically illustrated in the cut-away section at left in FIG. 1, the thick regions 42 comprise one or more elongate ridges 44 that extend from the wall structure 20 relative to adjacent thin regions 40. In some such examples, the one or more elongate ridges 44 extend transverse to the open top 14, that is, are not parallel to the open top 14.

The thickness of the thick regions 42 may have any suitable ratio relative to the thickness of the thin regions 40. As illustrative, non-exclusive examples, the thickness of the thick regions 42 may be in the range of 100-150%, 100-130%, 100-110%, 100-105%, or 105-120% of the thickness of the thin regions 40. Stated differently, the thick regions 42 may be 0-50%, 0-30%, 0-10%, 0-5%, or 5-20% thicker than immediately adjacent thin regions 40. Ratios outside of these ranges also are within the scope of the present disclosure. Moreover, the thickness of a thick region 42 may relate to a maximum or greatest thickness of a thick region 42, in so far as a thick region 42 may have more than one thickness across a span of a thick region 42.

In some examples, the thin regions 40 comprise 50-100%, 50-75%, 75-100%, or 75-95% of the wall structure 20. Similarly, in some examples, the thick regions 42 comprise 0-50%, 25-50%, 0-25%, or 5-25% of the wall structure 20.

In some examples, the thickness of thin regions 40 is generally constant across an entirety of the wall structure 20. In other examples, the thickness of thin regions 40 varies by less than 5%, 4%, 3%, 2%, or 1% across an entirety of the wall structure 20.

With continued reference to FIG. 1 and as discussed, in some examples of menstrual cups 10, the wall structure 20 comprises one or more elongate ridges 44. In some examples, the one or more elongate ridges 44 extend from the inner surface 24 of the wall structure 20. Additionally or alternatively, in some examples, the one or more elongate ridges 44 extend from the outer surface 22 of the wall structure 20. Elongate ridges 44 additionally or alternatively may be described as elongate bumps, elongate raised regions, elongate ribs, elongate spines, or raised bands.

In some examples, the one or more elongate ridges 44 are each continuous. That is, in some examples, the elongate ridges 44 do not have a longitudinal end, but rather encircle or surround a thin region 40. In some such examples, the one or more elongate ridges 44 may be described as encircling or circumscribing the wall structure 20, such as extending fully 360° around the longitudinal axis 26. In some examples, the one or more elongate ridges 44 are generally elliptical or ovular. In some examples, the one or more elongate ridges 44 consist of exactly two intersecting elongate ridges 44. In some examples, the one or more elongate ridges 44 comprise two or more intersecting elongate ridges 44, with FIG. 1 schematically representing two intersecting elongate ridges 44.

Figure 2:
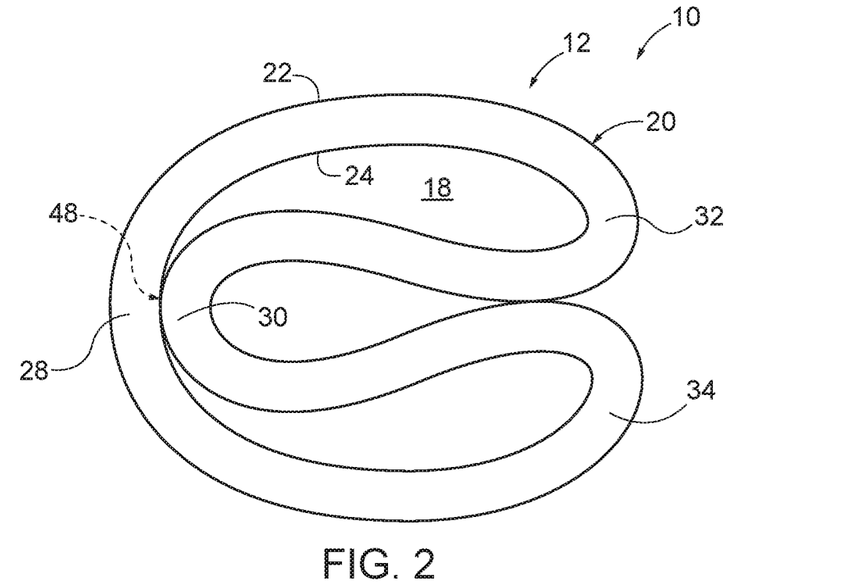
FIG. 2 is a schematic top view diagram representing menstrual cups according to the present disclosure in a folded conformation.

In some such examples, when the resilient body 12 is in the open conformation, the two or more intersecting elongate ridges 44 define two intersections that are directly opposite each other across the internal volume 18 of the resilient body 12 relative to the longitudinal axis 26. Moreover, in such examples, when the resilient body 12 is in the first folded conformation as discussed herein and as schematically represented in FIG. 2, the two intersections are positioned adjacent each other within the internal volume, such as at the region indicated at 48 in FIG. 2. Stated differently, the two intersections may be positioned at a vertex 48 of the generally C- or U-shaped cross-section of the resilient body 12. Additionally, in such examples, when the resilient body 12 is in the second folded conformation as discussed herein and as schematically represented in FIG. 3, the two intersections are positioned apart from each other within the internal volume 18, such as at the regions indicated at 50 and 52 in FIG. 3. Stated differently, the two intersections may be positioned at respective terminuses 50, 52 of the generally C- or U-shaped cross-section of the resilient body 12 when in a C-fold.

As discussed, some examples of menstrual cups 10 are configured to provide more than one degree, or level, of deformation of the open top 14 for unsealing the menstrual cup 10 from the walls of a vagina, depending on how the resilient body 12 is deformed by a user when the menstrual cup is operatively sealed with the walls of the vagina. In some such examples, the first location 36 coincides with an elongate ridge 44, and the second location 38 does not coincide with an elongate ridge 44. In some such examples, the first location 36 coincides with an intersection of two elongate ridges 44, such as schematically indicated in FIG. 1.

When present, elongate ridges 44 may have any suitable cross-section shape, with triangular and semi-circular cross-sections being illustrative, non-exclusive examples.

When present, elongate ridges 44 may have any suitable width, with illustrative, non-exclusive examples including widths in the range of 2-10, 2-8, 2-6, 2-4, 4-10, 4-8, 4-6, 6-10, 6-8, or 8-10 millimeters (mm). Similarly, elongate ridges 44 may have any suitable height, e.g., relative to directly adjacent regions of the wall structure 20, with illustrative, non-exclusive examples including heights in the range of 0.1-1, 0.1-0.7, 0.1-0.5, 0.1-0.3, 0.3-1, 0.3-0.7, 0.3-0.5, 0.5-1, 0.5-0.7, or 0.7-1 mm.

In some examples of menstrual cups 10, for a first span of the wall structure 20, cross-sections of the wall structure 20 that are parallel to the open top 14 (i.e., perpendicular to the longitudinal axis 26) have a uniform thickness, and for a second span of the wall structure 20, cross-sections of the wall structure 20 that are parallel to the open top 14 have a non-uniform thickness.

In some such examples, the first span is proximal to the open top 14 and the second span is distal to the open top 14. In other such examples, the second span is proximal to the open top 14 and the first span is distal to the open top 14.

In some examples, the first span accounts for 5-60%, 5-50%, 5-40%, 10-60%, 10-50%, 10-40%, 20-60%, 20-50%, 20-40%, or 20-30% of a total span of the wall structure 20 between the open top 14 and the closed bottom 16.

In some examples, the second span accounts for 40-95%, 50-95%, 60-95%, 40-90%, 50-90%, 60-90%, 40-80%, 50-80%, 60-80%, or 70-80% of a total span of the wall structure 20 between the open top 14 and the closed bottom 16.

In some examples of menstrual cups 10, the resilient body 12 and the wall structure 20 may be radially asymmetrical about the longitudinal axis 26. In other words, within at least a subset of cross-sections that are perpendicular to the longitudinal axis 26, at least one of the outer surface 22 and the inner surface 24 is not radially symmetrical with a uniform radius a full 360° relative to the longitudinal axis 26. In some such examples, the outer surface 22 of the wall structure 20 may be radially symmetrical about the longitudinal axis 26, while the inner surface 24 of the wall structure 20 is radially asymmetrical about the longitudinal axis 26. In other examples, the outer surface 22 of the wall structure 20 may be radially asymmetrical about the longitudinal axis 26, while the inner surface 24 of the wall structure 20 is radially symmetrical about the longitudinal axis 26. In yet additional alternative examples, both the outer surface 22 and the inner surface 24 of the wall structure 20 may be radially asymmetrical about the longitudinal axis 26. Additionally or alternatively, in some examples of menstrual cups 10, within at least a subset of cross-sections of the wall structure 20 that are perpendicular to the longitudinal axis 26, at least one of the outer surface 22 and the inner surface 24 are non-circular.

With continued reference to FIG. 1, some menstrual cups 10 further comprise an elongate stem 54 that extends from the closed bottom 16 away from the internal volume 18 of the resilient body 12 and that is coaxial with the longitudinal axis 26. In such examples, such as schematically represented in FIG. 1, the elongate stem 54 comprises one or more projections 56, which optionally may be spherical projections. When present, the projections provide additional structure and friction for a user to grasp the elongate stem 54 for operative removal of the menstrual cup 10 from the user's vagina. In some such examples, at least two, and optionally three, projections 56 are provided and vary from a larger diameter proximal the closed bottom 16 to a smaller diameter distal the closed bottom 16; however, other configurations of elongate stems 54 and optional projections 56 may be incorporated into a menstrual cup 10 according to the present disclosure.

Additionally, some menstrual cups 10 further comprise one or more vent holes 58 that extend through the wall structure 20 of the resilient body 12. In some such examples, the one or more vent holes 58 are closer to the open top 14 at the inner surface 24 than at the outer surface 22. Stated differently, the one or more vent holes 58 may be angled toward the open top 14. Accordingly, when the menstrual cup 10 is operatively sealed with the walls of the vagina, and a user imparts a force to the outer surface 24, air may be permitted to pass from external the menstrual cup 10 through a vent hole 58 and into the internal volume 18 to assist with releasing a seal between the menstrual cup 10 and the walls of the vagina. Moreover, in examples of menstrual cups 10, in which an intersection of two elongate ridges 44 is present, a vent hole 58 may be aligned with the intersection along a plane that contains the longitudinal axis 26, such as schematically represented in FIG. 1.

In some examples of menstrual cups 10, the resilient body 12 has a lip 60 that defines the open top 14, and in which the lip 60 is thicker than immediately adjacent portions of the wall structure 20. In some such examples, as optionally and schematically illustrated in FIG. 1, the lip 60 extends inward from the inner surface 24. Additionally or alternatively, in some examples, the lip 60 extends outward from the outer surface 22.

In some examples of menstrual cups 10, cross-sections of the wall structure 20 that are parallel to the open top 14 (and perpendicular to the longitudinal axis 26) have circular perimeters.

In some examples of menstrual cups 10, diameters of the wall structure 20 decrease from proximal the open top 14 to proximal the closed bottom 16.

In some examples of menstrual cups 10, a cross-section of the wall structure 20 containing the longitudinal axis 26 is generally U-shaped or parabolic. Resilient body 12 additionally or alternatively may be described as being generally bell-shaped.

Turning now to FIGS. 4-17, illustrative, non-exclusive examples of menstrual cups 10 in the form of menstrual cup 100 (FIGS. 4-10) and in the form of menstrual cup 200 (FIGS. 11-17) are illustrated. Where appropriate, the reference numerals from the schematic illustration of FIG. 1 are used to designate corresponding parts of menstrual cup 100 and menstrual cup 200; however, the examples of FIGS. 4-17 are non-exclusive and do not limit menstrual cups 10 to the illustrated embodiments of menstrual cup 100 and menstrual cup 200. That is, menstrual cups 10 are not limited to the specific embodiments of the illustrated menstrual cup 100 and menstrual cup 200, and menstrual cups 10 may incorporate any number of the various aspects, configurations, characteristics, properties, etc. of menstrual cups 10 that are illustrated in and discussed with reference to the schematic representations of FIGS. 1-3 and/or the embodiments of FIGS. 4-17, as well as variations thereof, without requiring the inclusion of all such aspects, configurations, characteristics, properties, etc. For the purpose of brevity, each previously discussed component, part, portion, aspect, region, etc. or variants thereof may not be discussed, illustrated, and/or labeled again with respect to menstrual cup 100 and menstrual cup 200; however, it is within the scope of the present disclosure that the previously discussed features, variants, etc. may be utilized with menstrual cup 100 and menstrual cup 200.

As seen in FIGS. 4-10, menstrual cup 100 is an example of a menstrual cup 10 that includes two continuous elongate ridges 44 extending from the inner surface 24 of the wall structure 20, with the two continuous elongate ridges 44 being elliptical in shape and intersecting each other at two opposed intersections 102. Moreover, the elongate ridges 44 of menstrual cup 100 have generally triangular cross-sections. The outer surface 22 of the wall structure 20 of menstrual cup 100 is smooth, and menstrual cup 100 includes a lip 60 that projects inward from the inner surface 24 of the wall structure. Moreover, menstrual cup 100 includes two vent holes 58 that are aligned with the two intersections of the two elliptical and continuous elongate ridges 44.

Menstrual cup 100 also is an example of a menstrual cup 10 that includes an elongate stem 54 with three spherical projections 56 that vary from a larger diameter to a smaller diameter from proximal the closed bottom 16 to distal the closed bottom 16.

Menstrual cup 100 has an internal volume 18 of about 38 mL.

Menstrual cup 200, shown in FIGS. 11-17, is similar in construction to menstrual cup 100, but has an internal volume 18 of about 30 mL. Like menstrual cup 100, menstrual cup 200 includes two continuous elongate ridges 44 extending from the inner surface 24 of the wall structure 20, with the two continuous elongate ridges 44 being elliptical in shape and intersecting each other at two opposed intersections 202. Like menstrual cup 100, the elongate ridges 44 of menstrual cup 200 have generally triangular cross-sections. The outer surface 22 of the wall structure 20 of menstrual cup 200 is smooth, and menstrual cup 200 includes a lip 60 that projects inward from the inner surface 24 of the wall structure. Additionally, menstrual cup 200 includes two vent holes 58 that are aligned with the two intersections of the two elliptical and continuous elongate ridges 44.

Also similar to menstrual cup 100, menstrual cup 200 is an example of a menstrual cup 10 that includes an elongate stem 54 with three spherical projections 56 that vary from a larger diameter to a smaller diameter from proximal the closed bottom 16 to distal the closed bottom 16.

Illustrative, non-exclusive examples of inventive subject matter according to the present disclosure are described in the following enumerated paragraphs:

A. A menstrual cup, comprising:

a resilient body having an open top and a closed bottom and defining an internal volume sized to hold menstrual fluid, wherein the resilient body comprises a wall structure that extends from the open top to the closed bottom, wherein the wall structure has an outer surface opposite the internal volume and an inner surface facing the internal volume, wherein the resilient body is biased to an open conformation, and wherein the resilient body has a longitudinal axis that extends through a center of the internal volume when in the open conformation.

A1. The menstrual cup of paragraph A, wherein the wall structure has:

two or more thin regions separated by one or more thick regions; or two or more thick regions separated by one or more thin regions;

wherein within the thin regions, the wall structure has a thin wall thickness within a first thickness range, wherein within the thick regions, the wall structure has a thick wall thickness within a second thickness range, and wherein the first thickness range is less than the second thickness range.

A1.1. The menstrual cup of paragraph A1, wherein the outer surface is smooth.

A1.2. The menstrual cup of any of paragraphs A1-A1.1, wherein the thick regions extend from the inner surface toward the internal volume relative to directly adjacent thin regions.

A1.3. The menstrual cup of paragraph A1, wherein the inner surface is smooth.

A1.4. The menstrual cup of any of paragraphs A1 and A1.3, wherein the thick regions extend from the outer surface away from the internal volume relative to directly adjacent thin regions.

A1.5. The menstrual cup of any of paragraphs A1-A1.4, wherein the thin regions comprise 1-10, 2-10, 4-10, 6-10, 2-6, 2-4, or 4-6 thin regions.

A1.6. The menstrual cup of any of paragraphs A1-A1.5, wherein the thin regions consist of 1, 2, 3, 4, 5, 6, 7, 8, 9, or 10 thin regions.

A1.7. The menstrual cup of any of paragraphs A1-A1.6, wherein the thick regions comprise 1-10, 2-10, 4-10, 6-10, 2-6, 2-4, or 4-6 thick regions.

A1.8. The menstrual cup of any of paragraphs A1-A1.7, wherein the thick regions consist of 1, 2, 3, 4, 5, 6, 7, 8, 9, or 10 thick regions.

A1.9. The menstrual cup of any of paragraphs A1-A1.8, wherein the thin regions comprise one or more elongate valleys extending into the wall structure relative to adjacent thick regions.

A1.9.1. The menstrual cup of paragraph A1.9, wherein the one or more elongate valleys extend transverse to the open top.

A1.9.2. The menstrual cup of any of paragraphs A1.9-A1.9.1, wherein the one or more elongate valleys are not parallel to the open top.

A1.10. The menstrual cup of any of paragraphs A1-A1.9, wherein the thick regions comprise one or more elongate ridges extending from the wall structure relative to adjacent thin regions.

A1.10.1. The menstrual cup of paragraph A1.10, wherein the one or more elongate ridges extend transverse to the open top.

A1.10.2. The menstrual cup of any of paragraphs A1.10-A1.10.1, wherein the one or more elongate ridges are not parallel to the open top.

A1.11. The menstrual cup of any of paragraphs A1-A1.10.2, wherein the thick wall thickness is in a range of 100-150%, 100-130%, 100-110%, 100-105%, or 105-120% of the thin wall thickness.

A1.12. The menstrual cup of any of paragraphs A1-A1.11, wherein the thick regions are 0-50%, 0-30%, 0-10%, 0-5%, or 5-20% thicker than immediately adjacent thin regions.

A1.13. The menstrual cup of any of paragraphs A1-A1.12, wherein the thin regions comprise 50-100%, 50-75%, 75-100%, or 75-95% of the wall structure.

A1.14. The menstrual cup of any of paragraphs A1-A1.13, wherein the thick regions comprise 0-50%, 25-50%, 0-25%, or 5-25% of the wall structure.

A1.15. The menstrual cup of any of paragraphs A1-A1.14, wherein the thin wall thickness is generally constant across an entirety of the wall structure.

A1.16. The menstrual cup of any of paragraphs A-A1.15, wherein the thin wall thickness varies by less than 5%, 4%, 3%, 2%, or 1% across an/the entirety of the wall structure.

A2. The menstrual cup of paragraph A, wherein the wall structure comprises one or more elongate ridges.

A2.1. The menstrual cup of paragraph A2, wherein the one or more elongate ridges extend from the inner surface.

A2.2. The menstrual cup of any of paragraphs A2-A2.1, wherein the one or more elongate ridges extend from the outer surface.

A2.3. The menstrual cup of any of paragraphs A2-A2.2, wherein the one or more elongate ridges are each continuous.

A2.4. The menstrual cup of any of paragraphs A2-A2.3, wherein the one or more elongate ridges encircle or circumscribe the wall structure.

A2.5. The menstrual cup of any of paragraphs A2-A2.4, wherein the one or more elongate ridges are generally elliptical or ovular.

A2.5.1. The menstrual cup of paragraph A2.5, wherein the one or more elongate ridges consist of two intersecting elongate ridges.

A2.6. The menstrual cup of any of paragraphs A2-A2.5.1, wherein the one or more elongate ridges comprise two or more intersecting elongate ridges.

A2.7. The menstrual cup of any of paragraphs A2-A2.6, wherein the one or more elongate ridges have a generally triangular cross-section.

A2.8. The menstrual cup of any of paragraphs A2-A2.7, wherein the one or more elongate ridges have a generally semi-circular cross-section.

A2.9. The menstrual cup of any of paragraphs A2-A2.8, wherein the one or more elongate ridges have a width in the range of 2-10, 2-8, 2-6, 2-4, 4-10, 4-8, 4-6, 6-10, 6-8, or 8-10 mm.

A2.10. The menstrual cup of any of paragraphs A2-A2.9, wherein the one or more elongate ridges have a height in the range of 0.1-1, 0.1-0.7, 0.1-0.5, 0.1-0.3, 0.3-1, 0.3-0.7, 0.3-0.5, 0.5-1, 0.5-0.7, or 0.7-1 mm.

A3. The menstrual cup of any of paragraphs A-A2.10,
wherein for a first span of the wall structure, cross-sections of the wall structure that are parallel to the open top have a uniform thickness; and
wherein for a second span of the wall structure, cross-sections of the wall structure that are parallel to the open top have a non-uniform thickness.

A3.1. The menstrual cup of paragraph A3, wherein the first span is proximal to the open top and the second span is distal to the open top.

A3.2. The menstrual cup of paragraph A3, wherein the second span is proximal to the open top and the first span is distal to the open top.

A3.3. The menstrual cup of any of paragraphs A3-A3.2, wherein the first span accounts for 5-60%, 5-50%, 5-40%, 10-60%, 10-50%, 10-40%, 20-60%, 20-50%, 20-40%, or 20-30% of a total span of the wall structure between the open top and the closed bottom.

A3.4. The menstrual cup of any of paragraphs A3-A3.3, wherein the second span accounts for 40-95%, 50-95%, 60-95%, 40-90%, 50-90%, 60-90%, 40-80%, 50-80%, 60-80%, or 70-80% of a/the total span of the wall structure between the open top and the closed bottom.

A4. The menstrual cup of any of paragraphs A-A3.4, wherein the resilient body is configured to be folded from the open conformation into:
a first folded conformation in which opposing sides of the wall structure are positioned generally adjacent each other and folded together along the longitudinal axis (e.g., such that the resilient body is deformed into a generally C- or U-shaped cross-section), wherein the wall structure imparts a first spring force in the first folded conformation; and a second folded conformation in which opposing sides of the wall structure are positioned generally adjacent each other and folded together along the longitudinal axis (e.g., such that the resilient body is deformed into a generally C- or U-shaped cross-section), wherein the wall structure imparts a second spring force in the second folded conformation, wherein the second spring force differs from (optionally is greater than) the first spring force, and wherein the opposing sides in the second folded conformation are offset (e.g., 90° or generally 90°) from the opposing sides in the first folded conformation.

A4.1. The menstrual cup of paragraph A4 when depending from paragraph A2.6, wherein in the open conformation, the two or more intersecting elongate ridges define two intersections directly opposite each other across the internal volume;

wherein in the first folded conformation, the two intersections are positioned adjacent each other within the internal volume generally (e.g., within a vertex of the generally C- or U-shaped cross-section); and wherein in the second folded conformation, the two intersections are positioned apart from each other within the internal volume (e.g., at respective terminuses of the generally C- or U-shaped cross-section).

A5. The menstrual cup of any of paragraphs A-A4.1, wherein at a first location on the outer surface of the wall structure a first distance away from the open top, impartation of a given force deforms the open top a first amount; and wherein at a second location on the outer surface of the wall structure the first distance away from the open top and spaced from the first location (e.g., by 90°) about the longitudinal axis, impartation of the given force deforms the open top a second amount, wherein the first amount is greater than the second amount.

A5.1. The menstrual cup of paragraph A5, when depending from paragraph A2, wherein the first location coincides with an elongate ridge, and wherein the second location does not coincide with an elongate ridge.

A5.2. The menstrual cup of any of paragraphs A5-A5.1 when depending from paragraph A2.6, wherein the two or more intersecting elongate ridges define at least one intersection, and wherein the first location coincides with an intersection of the at least one intersection.

A6. The menstrual cup of any of paragraphs A-A5.2, further comprising:

an elongate stem extending from the closed bottom away from the internal volume.

A6.1. The menstrual cup of paragraph A6, wherein the elongate stem comprises one or more spherical projections.

A6.1.1. The menstrual cup of paragraph A6.1, wherein the one or more spherical projections comprise at least two, and optionally three, spherical projections that vary from a larger diameter proximal the closed bottom to a smaller diameter distal the closed bottom.

A7. The menstrual cup of any of paragraphs A-A6.1.1, further comprising:

one or more vent holes extending through the wall structure.

A7.1. The menstrual cup of paragraph A7, wherein the one or more vent holes are closer to the open top at the inner surface than at the outer surface.

A7.2. The menstrual cup of any of paragraphs A7-A7.1 when depending from paragraph A2.6, wherein the two or more intersecting elongate ridges define at least one intersection, and wherein the one or more vent holes are aligned with respective ones of the at least one intersection along a plane that contains the longitudinal axis.

A8. The menstrual cup of any of paragraphs A-A7.2, wherein the resilient body has a lip that defines the open top, wherein the lip is thicker than immediately adjacent portions of the wall structure.

A8.1. The menstrual cup of paragraph A8, wherein the lip extends inward from the inner surface.

A8.2. The menstrual cup of paragraph A8, wherein the lip extends outward from the outer surface.

A9. The menstrual cup of any of paragraphs A-A8.2, wherein cross-sections of the wall structure that are parallel to the open top have circular perimeters.

A10. The menstrual cup of any of paragraphs A-A9, wherein diameters of the wall structure decrease from proximal the open top to proximal the closed bottom.

A11. The menstrual cup of any of paragraphs A-A10, wherein a cross-section of the wall structure containing the longitudinal axis is generally U-shaped or parabolic.

A12. The menstrual cup of any of paragraphs A-A11, wherein the wall structure is radially asymmetrical about the longitudinal axis.

A13. The menstrual cup of any of paragraphs A-A12, wherein the outer surface is radially symmetrical about the longitudinal axis and the inner surface is radially asymmetrical about the longitudinal axis.

A14. The menstrual cup of any of paragraphs A-A12, wherein the outer surface is radially asymmetrical about the longitudinal axis and the inner surface is radially symmetrical about the longitudinal axis.

A15. The menstrual cup of any of paragraphs A-A12, wherein the outer surface and the inner surface are radially asymmetrical about the longitudinal axis.

A16. The menstrual cup of any of paragraphs A-A15, wherein within at least a subset of cross-sections of the wall structure that are perpendicular to the longitudinal axis, at least one of the outer surface and the inner surface are non-circular.

A17. The use of the menstrual cup of any of paragraphs A-A16 to collect menstrual fluid within a vagina.

B. A method of folding the menstrual cup of any of paragraphs A-A16, the method comprising:

positioning opposing sides of the wall structure adjacent to each other; and folding the resilient body against itself along the longitudinal axis.

B1. The method of paragraph B when depending from paragraph A2.6, wherein the two or more intersecting elongate ridges define two intersections, and wherein the positioning comprises positioning the two intersections adjacent to each other.

B2. The method of paragraph B when depending from paragraph A2.6, wherein the two or more intersecting elongate ridges define two intersections, and wherein the positioning comprises positioning the two intersections apart from each other.

C. A method of releasing the menstrual cup of any of paragraphs A-A16 from a sealed configuration within a vagina, the method comprising:

imparting a force to the outer surface of the resilient body.

C1. The method of paragraph C when depending from paragraph A2, wherein the imparting comprises imparting the force against an elongate ridge of the one or more elongate ridges.

C2. The method of any of paragraphs C-C1 when depending from paragraph A2.6, wherein the two or more intersecting elongate ridges define at least one intersection, wherein the imparting comprises imparting the force against the at least one intersection.

As used herein, the term "configured" means that the element, component, or other subject matter is designed and/or intended to perform a given function. Thus, the use of the term "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being configured to perform a particular function may additionally or alternatively be described as being adapted to perform that function. Similarly, subject matter that is recited as being configured to perform a particular function may additionally or alternatively be described as being operative to perform that function.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

The invention claimed is:

1. A menstrual cup, comprising:
a resilient body having an open top and a closed bottom and defining an internal volume sized to hold menstrual fluid, wherein the resilient body comprises a wall structure that extends from the open top to the closed bottom, wherein the wall structure has an outer surface opposite the internal volume and an inner surface facing the internal volume, wherein the resilient body is biased to an open conformation, wherein the resilient body has a longitudinal axis that extends through a center of the internal volume when in the open conformation, wherein the wall structure comprises two or more intersecting elongate ridges, wherein the two or more intersecting elongate ridges extend from the inner surface, wherein the two or more intersecting elongate ridges are continuous and circumscribe the wall structure, and wherein the two or more intersecting elongate ridges are not parallel to the open top.

2. The menstrual cup of claim 1, wherein the two or more intersecting elongate ridges consist of two intersecting elongate ridges.

3. The menstrual cup of claim 1, wherein the two or more intersecting elongate ridges have a triangular cross-section.

4. The menstrual cup of claim 1, wherein the two or more intersecting elongate ridges have a semi-circular cross-section.

5. The menstrual cup of claim 1, wherein the two or more intersecting elongate ridges have a width in the range of 2-10 mm and a height in the range of 0.1-1 mm.

6. The menstrual cup of claim 1, wherein the resilient body is configured to be folded from the open conformation into:

a first folded conformation in which opposing sides of the wall structure are positioned generally adjacent each other and folded together along the longitudinal axis, wherein the wall structure imparts a first spring force in the first folded conformation; and
a second folded conformation in which opposing sides of the wall structure are positioned generally adjacent each other and folded together along the longitudinal axis, wherein the wall structure imparts a second spring force in the second folded conformation, wherein the second spring force differs from the first spring force, and wherein the opposing sides in the second folded conformation are offset from the opposing sides in the first folded conformation.

7. The menstrual cup of claim 6,
wherein in the open conformation, the two or more intersecting elongate ridges define two intersections directly opposite each other across the internal volume;
wherein in the first folded conformation, the two intersections are positioned adjacent each other within the internal volume generally; and
wherein in the second folded conformation, the two intersections are positioned apart from each other within the internal volume.

8. The menstrual cup of claim 1,
wherein at a first location on the outer surface of the wall structure a first distance away from the open top, impartation of a given force deforms the open top a first amount; and
wherein at a second location on the outer surface of the wall structure the first distance away from the open top and spaced from the first location by 90° about the longitudinal axis, impartation of the given force deforms the open top a second amount, wherein the first amount is greater than the second amount.

9. The menstrual cup of claim 8,
wherein the two or more intersecting elongate ridges define at least one intersection, and wherein the first location coincides with an intersection of the at least one intersection.

10. The menstrual cup of claim 1, further comprising:
an elongate stem extending from the closed bottom away from the internal volume, wherein the elongate stem comprises one or more spherical projections.

11. The menstrual cup of claim 1, further comprising:
one or more vent holes extending through the wall structure;
wherein the two or more intersecting elongate ridges define at least one intersection, and wherein the one or more vent holes are aligned with respective ones of the at least one intersection along a plane that contains the longitudinal axis.

12. A menstrual cup, comprising:
a resilient body having an open top and a closed bottom and defining an internal volume sized to hold menstrual fluid, wherein the resilient body comprises a wall structure that extends from the open top to the closed bottom, wherein the wall structure has an outer surface opposite the internal volume and an inner surface facing the internal volume, wherein the resilient body is biased to an open conformation, wherein the resilient body has a longitudinal axis that extends through a center of the internal volume when in the open conformation, wherein the wall structure comprises one or more elongate ridges, wherein the one or more elongate ridges extend from the inner surface, wherein the one or more elongate ridges are continuous and circumscribe the wall structure, wherein the one or more elongate ridges are not parallel to the open top, and wherein the one or more elongate ridges are elliptical.

13. A menstrual cup, comprising:
a resilient body having an open top and a closed bottom and defining an internal volume sized to hold menstrual fluid, wherein the resilient body comprises a wall structure that extends from the open top to the closed bottom, wherein the wall structure has an outer surface opposite the internal volume and an inner surface facing the internal volume, wherein the resilient body is biased to an open conformation, wherein the resilient body has a longitudinal axis that extends through a center of the internal volume when in the open conformation, wherein the wall structure comprises one or more elongate ridges, wherein the one or more elongate ridges extend from the inner surface, and wherein the one or more elongate ridges are continuous and circumscribe the wall structure, wherein the one or more elongate ridges are not parallel to the open top, wherein for a first span of the wall structure proximal to the open top, cross-sections of the wall structure that are parallel to the open top have a uniform thickness, and wherein the one or more elongate ridges are within a second span of the wall structure distal to the open top.

14. The menstrual cup of claim 13, wherein the first span accounts for 5-50% of a total span of the wall structure between the open top and the closed bottom.

15. A menstrual cup, comprising:
a resilient body having an open top and a closed bottom and defining an internal volume sized to hold menstrual fluid, wherein the resilient body comprises a wall structure that extends from the open top to the closed bottom, wherein the wall structure has an outer surface opposite the internal volume and an inner surface facing the internal volume, wherein the resilient body is biased to an open conformation, wherein the resilient body has a longitudinal axis that extends through a center of the internal volume when in the open conformation, wherein the wall structure comprises one or more elongate ridges, wherein the one or more elongate ridges extend from the inner surface, wherein the one or more elongate ridges are continuous and circumscribe the wall structure, and wherein the one or more elongate ridges are not parallel to the open top;
wherein at a first location on the outer surface of the wall structure a first distance away from the open top, impartation of a given force deforms the open top a first amount;
wherein at a second location on the outer surface of the wall structure the first distance away from the open top and spaced from the first location by 90° about the longitudinal axis, impartation of the given force deforms the open top a second amount, wherein the first amount is greater than the second amount; and
wherein the first location coincides with an elongate ridge, and wherein the second location does not coincide with an elongate ridge.

16. A menstrual cup, comprising:
a resilient body having an open top and a closed bottom and defining an internal volume sized to hold menstrual fluid, wherein the resilient body comprises a wall structure that extends from the open top to the closed bottom, wherein the wall structure has an outer surface opposite the internal volume and an inner surface facing the internal volume, wherein the resilient body is biased to an open conformation, wherein the resilient body has a longitudinal axis that extends through a center of the internal volume when in the open conformation, wherein the wall structure comprises one or more elongate ridges, wherein the one or more elongate ridges extend from the inner surface, wherein the one or more elongate ridges are continuous and circumscribe the wall structure, and wherein the one or more elongate ridges are not parallel to the open top; and
one or more vent holes extending through the wall structure, wherein the one or more vent holes are closer to the open top at the inner surface than at the outer surface.

17. A menstrual cup, comprising:
a resilient body having an open top and a closed bottom and defining an internal volume sized to hold menstrual fluid, wherein the resilient body comprises a wall structure that extends from the open top to the closed bottom, wherein the wall structure has an outer surface opposite the internal volume and an inner surface facing the internal volume, wherein the resilient body is biased to an open conformation, wherein the resilient body has a longitudinal axis that extends through a center of the internal volume when in the open conformation, wherein the wall structure comprises one or more elongate ridges, wherein the one or more elongate ridges extend from the inner surface, wherein the one or more elongate ridges are continuous and circumscribe the wall structure, wherein the one or more elongate ridges are not parallel to the open top, wherein the resilient body has a lip that defines the open top, wherein the lip is thicker than immediately adjacent portions of the wall structure, and wherein the lip extends inward from the inner surface.

18. A menstrual cup, comprising:
a resilient body having an open top and a closed bottom and defining an internal volume sized to hold menstrual fluid, wherein the resilient body comprises a wall structure that extends from the open top to the closed bottom, wherein the wall structure has an outer surface opposite the internal volume and an inner surface facing the internal volume, wherein the resilient body is biased to an open conformation, wherein the resilient body has a longitudinal axis that extends through a center of the internal volume when in the open conformation; and
one or more vent holes extending through the wall structure, wherein the one or more vent holes are closer to the open top at the inner surface than at the outer surface.

19. A menstrual cup, comprising:
a resilient body having an open top and a closed bottom and defining an internal volume sized to hold menstrual fluid, wherein the resilient body comprises a wall structure that extends from the open top to the closed bottom, wherein the wall structure has an outer surface opposite the internal volume and an inner surface facing the internal volume, wherein the resilient body is biased to an open conformation, wherein the resilient body has a longitudinal axis that extends through a center of the internal volume when in the open conformation, wherein the resilient body has a lip that defines the open top, wherein the lip is thicker than immediately adjacent portions of the wall structure, and wherein the lip extends inward from the inner surface and does not extend outward from the outer surface.

* * * * *